United States Patent
Tello et al.

(10) Patent No.: US 9,958,377 B2
(45) Date of Patent: May 1, 2018

(54) TESTING THE ADHESION OF ELASTIC ADHESIVES OR ELASTIC SEALING MATERIALS ON SURFACES OF COMPONENTS

(71) Applicant: Bombardier Transportation GmbH, Berlin (DE)

(72) Inventors: Waissi Tello, Ahnatal (DE); Helmuth Kleinoeder, Kassel (DE)

(73) Assignee: Bombardier Transportation GmbH, Berlin (DE)

( * ) Notice: Subject to any disclaimer, the term of this patent is extended or adjusted under 35 U.S.C. 154(b) by 81 days.

(21) Appl. No.: 14/912,497

(22) PCT Filed: Jul. 8, 2014

(86) PCT No.: PCT/EP2014/064607
§ 371 (c)(1),
(2) Date: Feb. 17, 2016

(87) PCT Pub. No.: WO2015/024700
PCT Pub. Date: Feb. 26, 2015

(65) Prior Publication Data
US 2016/0202174 A1   Jul. 14, 2016

(30) Foreign Application Priority Data
Aug. 22, 2013   (DE) .................. 10 2013 216 710

(51) Int. Cl.
*G01N 19/04*   (2006.01)
*G01N 33/32*   (2006.01)

(52) U.S. Cl.
CPC ............. *G01N 19/04* (2013.01); *G01N 33/32* (2013.01); *G01N 2203/0042* (2013.01); *G01N 2203/0091* (2013.01); *G01N 2203/0282* (2013.01)

(58) Field of Classification Search
CPC ....................................................... G01N 19/04
(Continued)

(56) References Cited

U.S. PATENT DOCUMENTS

| 2003/0054740 A1* | 3/2003 | Mansky | G01N 3/02 451/57 |
| 2012/0123700 A1* | 5/2012 | Tsaur | G01N 19/04 702/41 |

(Continued)

FOREIGN PATENT DOCUMENTS

| EP | 2431728 A2 | 3/2012 | |
| FR | 2572216 * | 4/1986 | G01N 19/04 |

(Continued)

OTHER PUBLICATIONS

Merkblatt (Bulletin) No. 1618, Jan. 2002, Deutscher Verbrand fur SchweiBen and verwandte Verfahren e.V. English translation attached; cited on p. 2 of specification.

(Continued)

*Primary Examiner* — Clayton E Laballe
*Assistant Examiner* — Kevin Butler
(74) *Attorney, Agent, or Firm* — The Webb Law Firm

(57) ABSTRACT

A method for testing the adhesion of elastic adhesives or elastic sealing materials on surfaces of components including: a) applying the adhesive/sealing material to a component surface, b) attempting by exerting a peeling force to detach the applied adhesive/sealing material from the component surface, and c) assessing the adhesion of the adhesive/sealing material on the basis of fractures caused in the adhesive/sealing material and the detachment of the adhesive/sealing material from the component surface by the exertion of the peeling force. Prior to and/or during step a), an anti-adhesion material layer is applied to at least one first part of the component surface, which causes poorer adhesion (Continued)

of the adhesive/sealing material to the component surface and therefore can be detached from the component surface with less peeling force than directly from the component surface.

9 Claims, 3 Drawing Sheets

(58) Field of Classification Search
USPC .......................................................... 73/150 A
See application file for complete search history.

(56) References Cited

U.S. PATENT DOCUMENTS

2013/0196106 A1* 8/2013 Erasmus ................. B32B 5/022
428/41.8
2016/0202174 A1* 7/2016 Tello ...................... G01N 19/04
73/150 A

FOREIGN PATENT DOCUMENTS

| FR | 2572216 A1 | 4/1986 |
| JP | 61155936 A | 7/1986 |
| JP | 62123551 U | 8/1987 |
| JP | 875634 A | 3/1996 |
| JP | 2002243629 A | 8/2002 |
| JP | 200963363 A | 3/2009 |

OTHER PUBLICATIONS

German industrial norm (DIN) 54457, Sep. 2007, published by Deutsches institut fur Normung e.V., Berlin; cited on p. 3 of specification.
European Standard EN ISO 10365, Aug. 1995, cited on p. 3 of the specification.

* cited by examiner

TESTING THE ADHESION OF ELASTIC ADHESIVES OR ELASTIC SEALING MATERIALS ON SURFACES OF COMPONENTS

CROSS-REFERENCE TO RELATED APPLICATIONS

This application is the United States national phase of International Application No. PCT/EP2014/064607 filed Jul. 8, 2014, and claims priority to German Patent Application No. 102013216710.5 filed Aug. 22, 2013, the disclosures of which are hereby incorporated in their entirety by reference.

BACKGROUND OF THE INVENTION

Field of the Invention

The invention relates to a method for testing the adhesion of elastic adhesives or elastic sealing materials on surfaces of components. The invention further relates to a corresponding arrangement for testing the adhesion.

Description of Related Art

Particularly in rail vehicle construction, different components are increasingly joined by adhesive bonding. Also particularly in rail vehicle construction, seals are used increasingly which are formed by elastic sealing materials that are applied to the surface of a component and adhere to the surface by adhesion. So therefore, the sealing materials are also adhesives but these are not used for the joining of two parts (components). So whenever the term adhesive is used in this specification and merely the adhesion of the adhesive to the surface of a single component is considered, the case of a sealing material is also considered by analogy. Except in the attached patent claims and individual passages of the specification, the term adhesive therefore includes sealing materials.

Depending on the adhesive properties when applied (viscosity, surface tension), the surface of the component (roughness, surface tension) and/or a required long-term resistance, substances may be applied before the application of the adhesive to the component surface to improve the adhesion of the adhesive on the component surface. These substances are particularly so called activating agents and/or primers. Activating agents are, in particular, cleaning solutions for pre-treating the component surfaces. A thin layer of the respective activating agent is, for example, applied to the component surfaces in one pass with a clean lintless cloth soaked with activating agent. For improving adhesion, it may be necessary to apply an undercoat on the component surface. That undercoat is the so called primer. The primer is normally applied by brush, melamine resin foams, felt bottle or other application devices. An evenly thin but complete coat of primer is applied.

The so called activating agents or primers are contact adhesion enhancing substances. In the following, when reference is made to adhesion promoters, the reference is in particular to activating agents and and/or primers.

The invention relates in particular to the thick layer bonding with elastic adhesives. These are defined as bonded joints whose bonding gap thickness is larger than 1.5 mm. The invention further relates particularly to adhesives which when set have rubbery properties and preferably permanently sustain (cyclical) shear deformation of more than 15% of the bonding gap thickness without suffering damage.

Such adhesive bonds and adhesives are, in particular, also the subject of Merkblatt (bulletin) No. 1618 (January 2002 of Deutscher Verband für Schweißen and verwandte Verfahren e.V. In Annex 3 of that Bulletin, a so called peel test/bead test is described for testing the adhesive and the bonded joint. For quality assurance and/or testing the long-term resistance under specific aging cycles (e.g., against the effect of moisture as described in that bulletin) the adhesion of the adhesive is tested and assessed on a component surface. The test specification explicitly also refers to sealing materials. For the test, a round bead of 10 mm diameter and a length of at least 50 mm is applied to the component surface. Also for establishing the long-term resistance, at least 50 mm are applied for each storage condition and test. When the adhesive has set, the adhesive bead is peeled off the component surface with needle-nosed pliers in longitudinal direction at an angle of 130° to 160° to the component surface.

If breaks of the adhesive material (so called cohesion fractures) form within the adhesive bead whilst peeling it off, this can lead to the tearing off of that part of the adhesive bead in which the peeling force (i.e., the force which pulls the adhesive off the component surface, i.e., the detachment force) is being applied by the needle-nosed pliers. A progressive cohesion fracture in any case results in that the peeling force (detachment force) initiated by the needle-nosed pliers acts increasingly weaker on the interface between the adhesive bead and the component surface. However, as the adhesion of the adhesive bead to the component surface will not only be tested and assessed at one place of the interface but at least along the said length of 50 mm, a cut with a sharp pointed knife is made at an angle to the surface normal of the component as deep as right into the material of the components and in this way the process of peeling off of the adhesive bead is assisted. The cut right into the material of the components is repeated approximately every 5 to 10 mm in longitudinal direction of the adhesive bead. A time gap of 3 seconds is to be maintained between the successive cuts made with the sharp pointed knife during which the adhesive material is continuously stressed by application of the peeling force. The cutting right into the material of the component is made particularly on painted or primed component surfaces. In that case the cut with the sharp pointed knife is made into the carrier substrate which is located beneath the coat of paint and primer, respectively. The layer structure on the component surface can consist of one layer or of several partial layers.

A similar method for testing the adhesion of an adhesive bead is described in the German industrial norm (DIN) 54457 (September 2007) published by Deutsches Institut für Normung e.V., Berlin.

After peeling off the adhesive bead, the so called fracture pattern is evaluated, particularly according to DIN EN ISO 10365. The higher the proportion of the peeling of the adhesive bead off the component surface caused by cohesion fractures in relation to the adhesion between the adhesive bead and the component surface, the better the adhesion of the adhesive to the component surface.

In painted or primed components, the cut with the sharp pointed knife is made into the carrier undercoat beneath the coat of paint and primer, respectively. This causes local damage of the paint structure and can lead to, e.g., corrosion phenomena unless the damaged local area is repainted and re-primed, respectively. Such a visible local damage is regarded as a deficiency of the object manufactured by customers and users.

The damage of the component surface is essential also with components containing a proportion of fiber, e.g., glass fiber reinforced plastic (GRP) materials. In these components, the cut is made right into fibers which can cause tearing out of fibers when the adhesive bead is peeled off and the fibers are finally exposed and therefore not sufficiently protected against the entry of moisture. Besides, the damage remains visible when the component is used again in normal production. Such a visible local damage is regarded as a deficiency of the object manufactured by customers and users.

Another object which is bonded with other components, particularly in rail vehicle construction, is a window pane. Placed on the edge of panes is normally a non-transparent coat of paint which is mostly applied to the edge of the pane by printing. Typically, the method applied is ceramic screen printing. The ink applied is damaged by the cutting with the sharp pointed object in the afore-described testing method and the damage remains visible when the component is used again in actual production. Such a visible local damage is regarded as a deficiency of the object manufactured by customers and users.

A disadvantage of the afore-described test method is the damage of the component by the sharp pointed knife. For avoiding damage to components used in the industrial production or in the crafting of objects, therefore, additional models were used. The models should have the same properties as the component to be glued, at any rate in relation to the area of the component surface and its interaction with the adhesive. The peeling test described above can then be made merely on the model.

However, the disadvantage of that is that the properties of the model may deviate from the properties of the component, especially because it cannot always be ensured that the preparation of a model proceeds under the same conditions as those under which the component is produced. Besides, this has the disadvantage that additional components must be procured as models. When the models are not treated in exactly the same manner as the components which are used in the production process, differences in the properties should be expected and additional production expenditure is caused, e.g., space needed for the place where adhesive is applied to the model. Higher expenditure is also required for making the model accompanying the production of the component under conditions as equally as possible.

SUMMARY OF THE INVENTION

An object of the invention is to reduce the expenditure for testing the adhesion of adhesives and of sealing materials to component surfaces. In particular, the above said disadvantages of the known test method shall be avoided.

According to an idea underlying the present invention, for preparing the testing of the adhesion of elastic adhesives or elastic sealing materials to component surfaces, at least a part of the component surface is provided with a material which, after the adhesive is applied to the component surface, is located between the adhesive and the component surface. The expression "at least a part of the component surface" is understood to mean that also more than a part of the component surface can be provided with the additional material. This is also preferred. In any case, the adhesive, after applying it to the component surface, is on both at least a (first) part provided with the additional material and also on at least a (second) part of the component surface in which the adhesive is in direct contact with the component surface. Whereas therefore the adhesive in the first part or the first parts is not directly in contact with the component surface and therefore cannot adhere directly to the component surface, the adhesive in the at least one second part has the direct contact required for testing the adhesion. Now when the adhesive extends continuously across the border between a first and a second part, the additional material, in the first part, performs the function of the sharp pointed knife from the afore-described known test method. This applies, in particular, when the additional material is selected such that the adhesion of the adhesive on the surface of the additional material is poorer than directly on the surface of the component or when the adhesion of the additional material on the component surface is poorer than that of the adhesive on the additional material. Poorer adhesion also includes the case that the adhesive and the material, respectively does not adhere at all. But it also applies that when a peeling force is applied to the adhesive (particularly the adhesive bead) that has a peeling effect in the first part, the additional material is detached from the component surface at a lower peeling force than is required for detaching the adhesive from the component surface in a neighboring second surface part. Consequently, therefore, the additional material can be referred to as anti-adhesion material in relation to the adhesion of the adhesive to the component surface.

In particular, the additional material is applied as anti-adhesion material coat to at least a first part of the component surface. For that, in particular, the thickness of the material layer is defined so thin that good wetting of the adhesive on the at least one second part is ensured and preferably less than one fifth and preferably less than one tenth of the thickness of the adhesive applied for testing the adhesion. The application of the anti-adhesion material layer offers the advantage that the course of the boundary surface between the adhesive applied to the additional material follows the course of the component surface and the process of peeling off the adhesives for the purpose of testing the adhesion can be performed in the same way as with the known method.

In any case, the use of an anti-adhesion material in the at least first part offers the advantage already suggested above that the detachment of the adhesive without the use of a sharp pointed object in the first part is facilitated and thereby a peeling force can be exerted in spite of or prior to the occurrence of a cohesion fracture in the adhesive which has a detaching effect on the adhesive in a second part of the component surface adjoining the first part. Damage to the component surface by a sharp pointed object is thus avoided. Otherwise the test can be performed particularly exactly as described above or in the norms and the technical bulletin cited above.

In particular, the adhesive applied to the different parts of the component surface can extend continuously across at least one border between a first part and a second part of the component surface, e.g., in a longitudinal direction, such as in the form of an adhesive bead extending in the longitudinal direction. The longitudinal direction is, in particular, a straight direction. The peeling force exerted on the adhesive which acts as detaching the adhesive from the surface, is exerted particularly (as with the known test method) in such a way that one component of the peeling force acts in the longitudinal direction and another component of the peeling force has a detaching effect perpendicular to the surface of the component. As aforementioned, the longitudinal direction in that case extends across one border or across several borders between a first and a second part each of the component surface. Preferably, the longitudinal direction extends across an at least first part the edges of which that are located opposite each other adjoin a second part of the component surface.

In particular, the following is contemplated: A method for testing the adhesion of elastic adhesives or elastic sealing materials on surfaces of components, comprising the following steps:
- a) The adhesive or the sealing material is applied to the component surface of a component,
- b) It is attempted, optionally after curing of the adhesive or sealing material, by exerting a peeling force, to detach the applied adhesive or the applied sealing material from the component surface, and
- c) On the basis of fractures caused in the adhesive or the sealing material by the exertion of the peeling force, on the one hand, and the detachment of the adhesive or the sealing material from the component surface by the exertion of the peeling force, on the other hand, the adhesion of the adhesive or the sealing material is assessed.

Prior to and/or during step a), an anti-adhesion material layer is applied to at least one first part of the component surface, which causes poorer adhesion of the adhesive or the sealing material to the component surface and therefore the adhesive or the sealing material can be detached from the component surface by a lower peeling force than from the component surface directly. The adhesive or the sealing material is applied in step a) as a continuous material section both to the at least one first part of the component surface to which the anti-adhesion material layer is and/or was applied and directly to at least one second part of the component surface.

Further, it is contemplated: An arrangement for testing the adhesion of elastic adhesives or elastic sealing materials to surfaces of components, with adhesive or sealing material applied to a component surface of a component, and with an anti-adhesion material layer because of which the adhesion of the adhesive or the sealing material to the component surface is poorer and can therefore be detached from the component surface by applying a lower peeling force than directly from the component surface, wherein the adhesive or the sealing material is applied, as continuous material section, both to at least one first part of the component surface with anti-adhesion material layer between the adhesive and the component surface and also directly to at least one second part of the component surface without anti-adhesion material layer.

Curing of the adhesives as used herein means, in particular, the said setting. Elastic adhesives are, particularly in the case of thick layer bonding, typically applied to the component surface in highly viscous state. As a rule, one-component, moisture-setting polyurethane adhesives, silane terminated polyethers, silane modified polyurethanes, accelerated polyurethane systems (so called booster adhesives) or silicone systems have the required elastic properties for the bead peeling test. However, the invention is not restricted to the above adhesive systems but merely refers to the required elastic properties after setting of the adhesive and sealing material, respectively as is already defined in the prior-art test method. To enable the setting, it may be necessary for certain embodiments of adhesives to mix two components with each other.

The adhesive is particularly applied to the component surface in the same way as in the prior-art test method. For example, the adhesive may be pressurized in a cartridge and delivered from an opening in the cartridge. Alternately the adhesive may be conveyed into the area at the component surface by a dosing system with pump technology (e.g., scoop piston pump and/or gear pump). The emerging adhesive is applied to the required area of the component surface. Other tools, e.g., a spatula, can be used for application to the component surface.

Depending on the component surface, the long-term stress and the elastic adhesive or sealing material, adhesion-promoting substances, so called activating agents and/or primers, may be required for good adhesion that may be applied to the component surface after cleaning as adhesion promoters for the elastic adhesive or sealing material. This is already known in principle. In particular, therefore, taking place optionally before the application of the adhesives in the first part of the component surface and/or in the second part if the component surface are:
- i) a cleaning and/or mechanical surface preparation (e.g., grinding or blasting in case of metal surfaces) of the component surface and/or
- ii) an application of at least one adhesion-promoting substance to the component surface.

The anti-adhesion material layer can be applied to the component surface in the at least first part prior to, during or after step i) and/or prior to, during or after step ii). Preferably an anti-adhesion material is used which, after step c), makes residue-free detachment from the component surface possible. The anti-adhesion material layer is applied preferably after step i) and/or step ii) to component surfaces which permit the testing of the adhesion outside the direct bonding area.

As with the prior-art test method, the peeling force on the cured adhesive is preferably applied by needle-nosed pliers. In particular, the shape of the cured adhesive is that of an adhesive bead.

It happens with the method of the prior art described above that the applied peeling force is insufficient for further peeling off the adhesive, particularly the adhesive bead, so that cutting down to the adhesive surface with a sharp pointed object is again necessary for further peeling off of the adhesive bead. The invention produces relief because a peeling force that is sufficient for detachment can be exerted on the adhesive at a first part of the component surface, particularly by again applying a tool (e.g., needle-nosed pliers). In the first part, the peeling force exerted on the adhesive leads to an enforced detachment of the adhesive from the anti-adhesion material and/or a detachment of the anti-adhesion material from the component surface due to the reduced adhesion. As the detachment of the adhesive from the first part advances, the peeling force also acts in an adjacent second part.

In particular, one embodiment of the invention is based on a predefined length of a first part with anti-adhesion material layer between two second parts without anti-adhesion material layer. The distance of the second parts to each other ensures that the peeling force—in spite of the absence of a cut into the adhesive by means of a sharp pointed object—can be exerted on the adhesive in otherwise the same manner as with the prior-art test method. The peeling force can be exerted successively on the adhesive in the second parts. For example, the peeling force is at first exerted on the adhesive in one of the second parts and it can be stated in that way to what degree the adhesive in that second part produces a detaching action. If with the progressing detachment of the adhesive from that second part the peeling force exerted should not be sufficient for the further peeling off of the adhesive, particularly the adhesive bead, the peeling force can now be exerted on the adhesive in the first part and with the progressive detachment of the adhesive from the first part also to the other second part.

In particular, therefore, the adhesive or the sealing material can be applied to the component surface in such a manner that the adhesive or the sealing material extends, in a longitudinal direction, at least from one of the second parts over one of the first parts to one of the second parts. In particular, the adhesive or the sealing material extends, in the longitudinal direction, at least from one of the second parts over one of the first parts to another one of the second parts. However, the two second parts can also be connected to each other, such as by a part that extends parallel to the longitudinal direction.

As also with the prior-art test method, e.g., in the case of an adhesive bead, the peeling force can comprise of a force component that acts in the longitudinal direction of the adhesive At the start of the application of a peeling force to the adhesive the peeling force is induced preferably in the adhesive, where a first part is located. The subsequent application of a peeling force to the adhesive in an adjacent second part is facilitated by this. Also, no cut into the adhesive to the substrate is required at the beginning of the peeling process so that the peeling off of the adhesive is enabled.

By applying the peeling force to the adhesive at the said second part a force is exerted on the adhesive which, depending on the strength of adhesion of the adhesive, can produce an effect of detachment from the second part. Thus, a test of the adhesion of the adhesive takes place in that second part. Particularly as with the test method of the prior art, the strength of the peeling force is increased continuously and/or in steps until, within the adhesive, a cohesion fracture and/or a detachment of the adhesive from the second part occurs. In this way, the adhesion of the adhesive to the second part can be assessed. A detachment of the adhesive, should it occur, would be in longitudinal direction. When the detachment reaches the borderline between the second part and the first part, the detachment progresses when the action of the peeling force continues and detaches the adhesive also from the first part. The reason for that is the poorer adhesion of the adhesive to the first part and/or the absence of, or poor, adhesion of the anti-adhesion material layer to the first part of the component surface. Should a cohesion fracture occur within the adhesive and progress to a point at which the force causing the detachment is becoming lower, the tensile force can be applied to the adhesive at another point, particularly near the borderline between the second part and the first part or to the first part. Hence, it is possible in a simple way, after the detachment or the attempted attachment of the adhesive from the second part and without use of a sharp tool which peels the adhesive off the component surface, to induce a potentially detaching peeling force in the adhesive also in such a way that it acts in the second part disposed opposite as seen in longitudinal direction from the first part.

In preferred embodiment, the adhesive or the sealing material is/is being applied to the component surface in such a way that the adhesive or the sealing material extends, in the longitudinal direction, over first and second parts of the component surface disposed alternately in succession.

In that embodiment, particularly the afore described process of inducing a peeling force in the adhesive can be performed across several second parts. Thus, as with the prior-art test method, the adhesion of the adhesives to the component surface can be tested over a stretch of sufficient length.

Preferably, the distances of the first parts defined in longitudinal direction by the dimensions of the second parts are of equal size. This creates the same preconditions for the different second parts for testing the adhesion of the adhesive. Thus it can be assessed reliably whether the adhesion of the adhesive at the different second parts of the component surfaces is good or different.

After performing the test method, adhesive (optionally after application of an adhesion-promoting substance to the component surface) can again be applied to the same parts (including the at least one second part but without the anti-adhesion material layer) and thereby an adhesive bond or a seal produced in the manufacture of an object.

With a cohesion fracture proportion of a predefined minimum percentage (e.g., of 75%) on the tested surface formed by the second parts, the adhesion is good or sufficient as also with the prior-art test method. Such a successfully tested component surface makes it possible to again or further use the component for actual production. A cohesion fracture proportion of a certain percentage means that that percentage of the tested surface is covered with adhesive as before.

For the reuse of the successfully tested component the cohesion fracture proportion of the adhesive (that is, the remaining adhesive residue) is preferably not removed from the tested surfaces. The anti-adhesion material layer, however, is removed completely from the component surface. Thereafter it is possible again to apply adhesive or sealing material of the same type to the first and second parts (but without anti-adhesion material layer on the first parts) and in this way to produce an adhesive bond or a seal between two components.

That renewed application of adhesive also on adhesive residue is practiced particularly after a treatment of the adhesive residue with an adhesion-promoting agent (also referred to as activating agent). Thus, the adhesive residue remaining on the tested surfaces can be "reactivated" by activating agents according to the instructions of the adhesive manufacturer with the result that again adhesive or sealing material of the same type can be applied to the remaining "activated" adhesive residue and in this way an assembly of the successfully tested component can be made possible. This approach is a common method when window panes are replaced after an accident. After the accident, the bonded joint of the window pane, for example, to a body of a rail vehicle is cut open by oscillating blades but is not removed from the surface. A new window pane is finally bonded to the car body with the reactivated adhesive residue. With this known method also the adhesive residues are not removed.

With component surfaces on which a test of the adhesion is only possible on the direct adhesive area that is actually intended for the assembly of the component (e.g., ceramic screen printing edge of window panes) it is absolutely necessary to use anti-adhesion materials for which it can be demonstrated that they can be peeled off the component surface without residue. If the anti-adhesion materials are applied prior to or after step a), the further processing of the component surfaces at the first parts also starts with step a) again. When the anti-adhesion materials can demonstrably be peeled off without leaving residue and the anti-adhesion materials are applied after step b), the first parts already treated with adhesion promoters are "reactivated" in accordance with the instructions of the adhesive manufacturer for further use with specific adhesion promoters (possibly other agents than the adhesion promoters intended for the treatment of the actual component surface). Further use is finally possible after "reactivation" of the first parts and the adhesive residue.

With component surfaces that permit a test of the adhesion on other parts than the parts intended for assembly (e.g., non-transparent component where the residues from testing such as adhesive residues are not visible after the component is installed), it is preferred to test in these other parts. Unlike the case described above, it is not necessary in that case to remove the anti-adhesion material from the component without residue. In fact, optionally again after a pretreatment, adhesive or sealing material of the same type can again be applied but to other parts of the component surface than the first and second parts and in that way an adhesive bond or a seal between two components obtained.

Even if the adhesive or sealing material of the same type is applied to other parts of the component surface than previously during the test procedure the test can produce reliable information about the adhesion of the adhesive to the component surface. This applies particularly when the whole component surface at which the test is performed and to which adhesive or sealing material is applied again for producing an adhesive bond are shaped alike.

In particular, the anti-adhesion material layer can be a material layer that already exists before the application of the anti-adhesion material to the component surface. This has the advantage that the time needed for application to the component surface is shortened and an anti-adhesion material layer of the same type and thickness can be applied to the complete first part or to the complete first parts.

Preferably, the prefabricated anti-adhesion material layer has an adhesive film at least on one side. Thus it is possible to use, e.g., so called adhesive tapes. In particular, therefore, glued to the at least one first part is an area of the anti-adhesion material of the same size, in that the adhesive layer provided on the anti-adhesion material layer is used for gluing. Finally, therefore, that adhesive layer is disposed between the actual component surface and the surface formed by the anti-adhesion material to which the adhesive is applied for testing.

In particular alternative to the use of adhesive tapes as anti-adhesion material layer a prefabricated anti-adhesion material layer can be used which, however, is not completely covered with an adhesive layer. This anti-adhesion material layer is applied to the component surface in preferred manner such that it extends, in strip shape, transversely to the longitudinal direction of the later applied adhesive to be tested. Therein, the anti-adhesion material layer extends over a width transversal to the longitudinal direction that is wider than the width of the applied adhesive that is to be tested. In particular, the anti-adhesion material layer extends, on both sides, over the area to which the adhesive to be tested is applied. Further, it is preferred that the anti-adhesion material layer is fixed, e.g., by adhesive tape, on the component surface across the width laterally next to the areas intended for the adhesive to be tested.

Such an anti-adhesion material layer may, e.g., be a strip-shaped cable tie that is normally used for binding several electrical cables together. Adhesive tape, for example, can be used for laterally fixing the anti-adhesion material layer. Alternately, strips of prefabricated plastic sheet can be used as anti-adhesion material layer. Pieces, strips, in particular, of anti-adhesion material layer can also be made of cardboard or paper. The use of lintless paper or lintless cardboard is preferred. Pieces of the anti-adhesion material layer can also be made, in particular, cut, from aluminum foil or foam sheet. The foam sheet is, for example, melamine resin foam. Furthermore, preferably strip-shaped PTFE (polytetrafluoroethylene) is a suitable anti-adhesion material.

Another possibility of making and preparing, respectively, the first and second parts for the test procedure is the use of a stencil. The stencil can be formed of the anti-adhesion material and/or used for applying anti-adhesion material to areas of the component surface predefined by the stencil. It is preferred that the stencil is formed by a material layer that is, e.g., not thicker than 1 mm. Provided in the stencil are holes which are preferably of strip shape and, e.g., the strips being of equal length run parallel to and at a constant distance to one another.

If—as preferred—the stencil is formed of anti-adhesion material, the stencil can be placed on the component surface and/or fixed to the component surface or is provided with an adhesive film all around so that the stencil covers the component surface with the exception of the area of the holes. Now the adhesive to be tested can be applied to the stencil so that it extends continuously over first parts covered by the stencil and over cut-out second parts.

Alternately the stencil can be applied to the component surface and/or fixed to the component surface and/or is provided with an adhesive film all around and anti-adhesion material can be applied to the cut-out areas of the stencil. Thereafter the stencil is removed from the component surface and the anti-adhesion material applied to the cut-out areas of the component surface remains on the component surface. After that, the adhesive to be tested can be applied to the component surface so that it extends at least across one area provided with anti-adhesion material. In particular, the stencil can be made of the said anti-adhesion materials. Further, it is possible to design the holes running parallel to each other in the stencil wide enough so that they are at least as wide as the adhesive to be tested. The material of the stencil can form the borders of the cut-out areas at opposite ends of the stencil. Preferably, the stencil is provided with an adhesive film on one side and can thus be fixed to the component surface. Alternately the areas of the stencil forming the borders of the cut-out areas on the opposite sides are fixed, e.g., glued to the component surface. Additional adhesive tapes can be used for that.

As result of the assessment of the adhesion of the adhesive or the sealing material the decision can be made that the component may be used for production. If the adhesion of the adhesive to the component surface is insufficient, it can be decided that the component may not be used in production.

In this way, in particular, the use of additional models which are a priori not intended for production can be avoided. In particular, damage by sharp pointed tools as used in accordance with the known test method is avoided. So, unlike additional models, the components used for the test method are not different from the components used in production. Cost for additional models is not incurred.

Furthermore, distances between the two parts of the component surface to which the adhesive is applied directly can be specified. Thus, unlike the use of a sharp pointed knife according to the test method of the prior art, the distances need not be defined during the test. Thus by specifying the size of the first parts that space the second parts apart from one another the test conditions of different test procedures are becoming comparable. Besides, the likeliness of an inaccurate performance of the prior-art test method is higher than the method with first and second parts proposed herein. The prior art test method implies the risk that the cuts are not made properly down to the adhesive surface and that the cut may be made at a high state of stress of the adhesive bead, which can lead to local flaking of paint in painted samples or components.

In the case of the said window panes, the test method enables the test to be made at the edge of the pane where a non-transparent paint coat is located and the pane is to be glued.

BRIEF DESCRIPTION OF THE DRAWINGS

The invention will now be described with reference to the accompanying drawings.

DETAILED DESCRIPTION OF THE INVENTION

Figure 1:
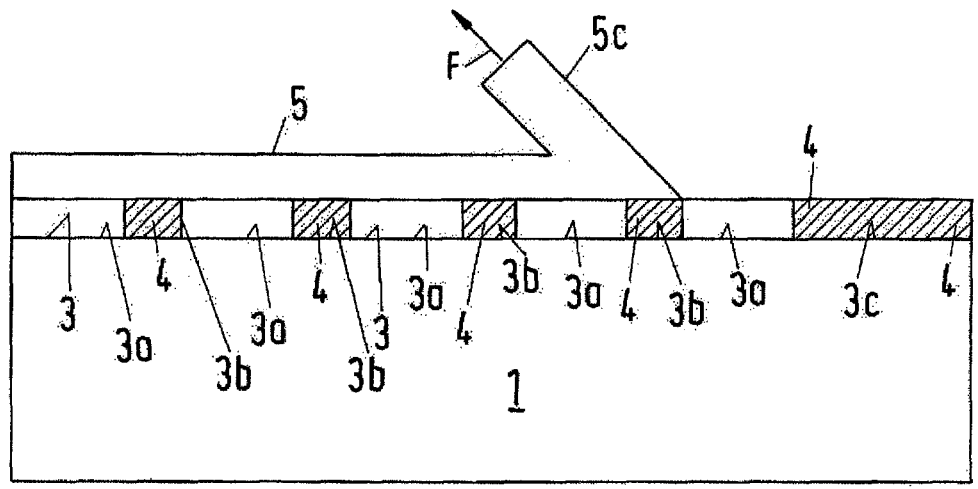
FIG. 1 is a schematic view of a part through a component with an adhesive applied to the component surface, wherein first parts of the component surface are provided with an anti-adhesion material so that the anti-adhesion material is disposed between the adhesive and the component surface.

FIG. 1 is a not true-to-scale representation of a component 1 forming a component surface 3 on its upper side that is flat in the concrete embodiment of the innovation. The component surface 3 extends in horizontal direction in the figure. Applied to first parts 3b, 3c of the component surface 3 is an anti-adhesion material layer 4. For better visibility, the height and thickness, respectively of the anti-adhesion material layer 4 is widely overstated in the figure. Applied to the first parts 3c shown on the right in FIG. 1 is the same type of anti-adhesion material as is to the other first parts 3b. But the first part 3c is longer (in the longitudinal direction from right to left) than the other first parts 3b so that the adhesive can be detached with little peeling force. For example, the adhesive in the first part 3c is detached in simple manner by needle-nosed pliers so that it can be peeled off the component surface over the following (towards the left in FIG. 3) first 3b and second 3a parts. As regards the use of needle-nosed pliers, the method presented here is not different from the prior art method.

Disposed between and beside the first parts 3b, 3c are the second parts 3a which are not covered by the anti-adhesion material layer 4. The thickness of the anti-adhesion material layer 4 is approximately constant in the first parts 3b, 3c.

Applied to the first parts 3b, 3c and to the second parts 3a is adhesive 5 in the form of an adhesive bead, the adhesion of which to the component surface 3 shall be tested. The adhesive bead is of oblong shape in the said longitudinal direction.

Figure 2:
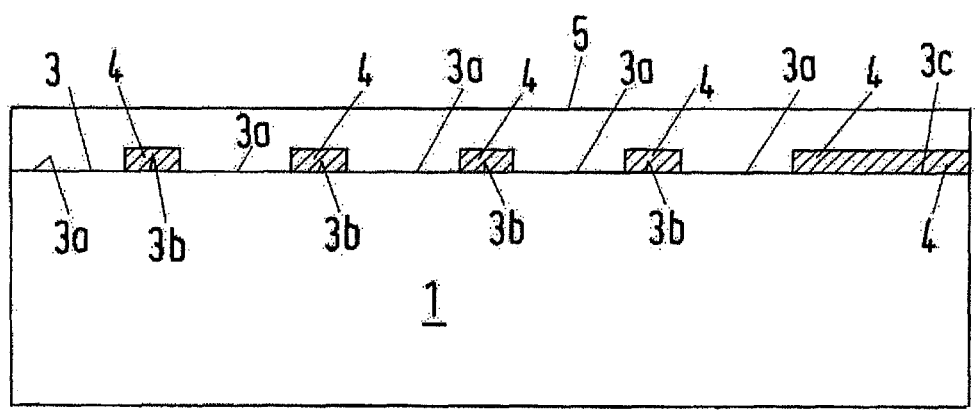
FIG. 2 is a view as in FIG. 1, wherein in can be seen that the adhesive outside the first parts is in direct contact with the component surface in second parts of the component surface.

FIG. 2 shows the arrangement from FIG. 1, wherein the thickness of the anti-adhesion materials 4 is less overstated and wherein it can be seen that the adhesive 5 extends between the anti-adhesion material layer 4 to the second parts 3a of the component surface 3.

Figure 3:
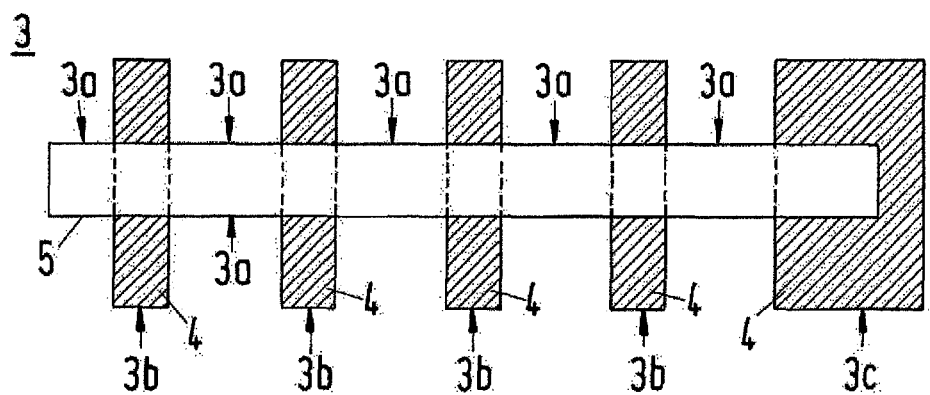
FIG. 3 is a schematic top view of the arrangement in FIG. 1 and FIG. 2.

The top view of FIG. 3 shows that the anti-adhesion material layer 4 extends, in strip shape, transverse to a longitudinal axis of the adhesive 5 running horizontally in FIG. 3. The width of the strips of the anti-adhesion material 4 in the vertical direction of FIG. 3 is larger than the width of the adhesive 5. The anti-adhesion material layer 4 extends on both sides (above and below in the illustration of FIG. 3) of the adhesive 5. The anti-adhesion material layer 4 covers the first parts 3b, 3c of the component surface 3. Disposed between the first parts 3b are the second parts 3a of the component surface 3, on which the adhesive 5 contacts the component surface directly, without anti-adhesion material layer 4 in-between.

In one embodiment of the test method, at first the anti-adhesion material is applied to the first parts 3b, 3c of the component surface 3. Optionally the anti-adhesion material layer 4 is bonded to the first parts 3b, 3c, e.g., by an adhesive layer on the underside of the anti-adhesion material or by adhesive tape not shown in FIG. 3 applied laterally of the adhesive to be tested. In particular in components in which the adhesion of the adhesive must be tested on the bonding surface later to be used in production (such as, e.g., window panes), the adhesive strips can be fixed laterally to the component surface 3 to be tested, beyond the fringes of the anti-adhesion material strip 4. In particular, it can be avoided in this way that adhesive strips for fixing the anti-adhesion material 4 and/or an adhesive at the underside of the anti-adhesion material 4 by which the anti-adhesion material 4 is fixed to the component surface is/are bonded to the area that is later used for bonding in production. Alternately that is also possible provided it can be demonstrated that the residue-free detachment or a possibility for subsequent cleaning (e.g., with solvent cleaners) of these areas exists.

After the application of the anti-adhesion material layer 4, the adhesive 5 is applied as adhesive bead in the concrete embodiment as can be seen in the top view of FIG. 3. The adhesive bead is, e.g., of semicircular cross-part, i.e., its upper part forms the semicircular shape in the cross part whereas the adhesive rests on the, e.g., approximately flat base each above the first parts 3b, 3c and on the second parts 3a.

After curing of the adhesive 5, a peeling force F, as shown schematically in FIG. 1, is exerted on the adhesive 5 in a direction that includes an angle from 130° to 160° to the longitudinal direction (FIG. 1). The longitudinal direction therein is defined, in FIG. 1, as the direction extending longitudinally to the extension of the adhesive 5 from left to right in the figure. When the peeling force F is exerted on the right area in FIG. 1, the peeling force F can detach the adhesive 5 towards the left from the component surface if the adhesion of the adhesive permits that. Otherwise increasing the peeling force F leads to a cohesion fracture in the adhesive. The first part 3c shown on the right in FIG. 1, with anti-adhesion material layer 4 disposed on it, in the state shown in FIG. 1, has made detachment of the end part 5c of the adhesive 5 possible. Furthermore, the peeling force F has detached the end part 5c completely from the second part 3a of the component surface 3 shown on the extreme right in FIG. 1. Hence, the adhesion of the adhesive 5 is insufficient.

An attempt is made, however, to detach the adhesive 5 also from the other remaining parts of the component surface 3 in order to test the adhesion of the adhesive 5 to the other second parts. Because the adhesive action of the adhesive 5 to the anti-adhesion material layer 4 and/or the adhesive action of the anti-adhesion material 4 to the component surface is poor, the adhesive 5, in the further test procedure, is detached in the (seen from right) second first part 3b from the anti-adhesion material layer 4 and/or the anti-adhesion material layer 4 from the component surface and the peeling force F then acts on the boundary surface between the adhesive 5 and the second of totally five illustrated second parts 3a of the component surface 3. This is no more seen in FIG. 1, but is illustrated for explaining another procedure of the test in FIG. 7. Then it can be observed again whether cohesion fractures within the adhesive 5 or the detachment of the adhesive 5 from the second part 3a of the component surface 3 dominate.

When the adhesive bead shown in FIG. 1 has completely (except for any residue remaining on the component surface 3) been detached from the component surface 3, the result of the detachment is assessed with consideration of cohesion fractures at the second parts 3a. A cohesion fracture proportion of at least 75% of the total share of the second parts is rated as good adhesion of the adhesive to the component surface. This also corresponds to the evaluation method of the prior art test method.

Figure 5:
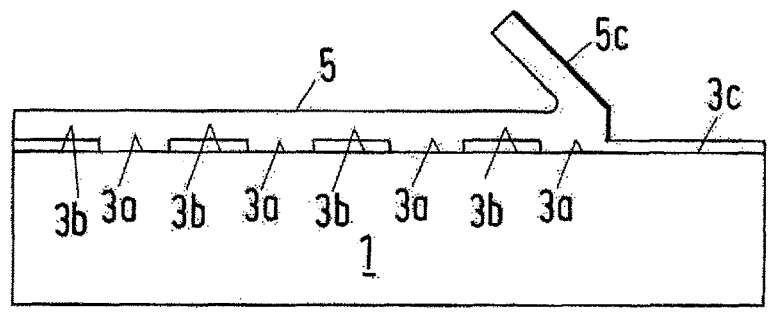
FIGS. 5-7 are a view similar to that in FIGS. 1 and 2, showing different states during the test process in which the adhesive is detached from the component surface.
Figure 6:
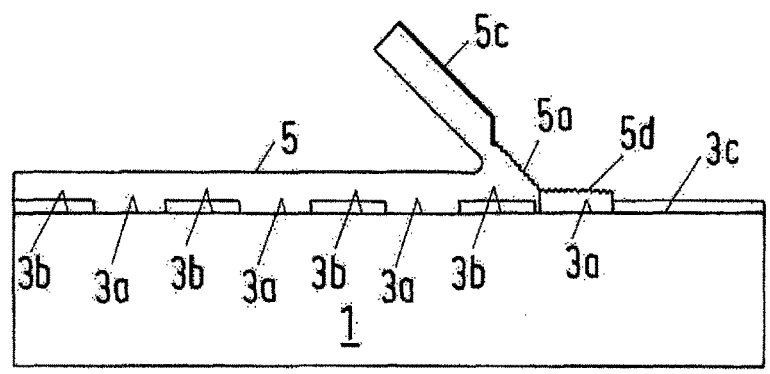
Figure 7:
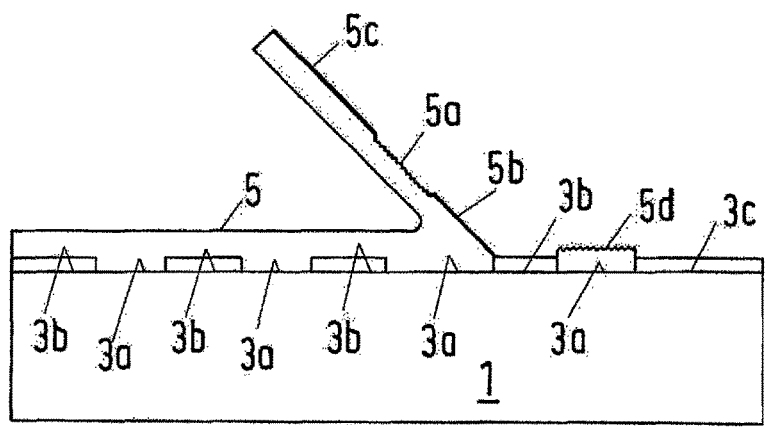

FIGS. 5 to 7 illustrate another example of the test procedure based on the schematic presentation of the starting situation in FIG. 2. As already described before with reference to FIG. 1, the peeling force F is at first exerted on the adhesive 5 at the first part 3c of the component surface. This again results in the complete detachment of the end part 5c of the adhesive 5 from the first part 3c without the necessity of a cut through the adhesive 5 right into the component surface. The state obtained by this is shown in FIG. 5.

Now the peeling force F is exerted on the adjoining second part 3a at which no anti-adhesion material is arranged. Seen from right in FIGS. 5 to 7, that part 3a can be referred to as the first of the second parts 3a. As FIG. 6 shows although the adhesive 5 is detached from that part 3a, an adhesive residue 5d remains on the component surface on the entire length of that part 3a. Accordingly, the detached adhesive bead comprises a cohesion fracture 5a. The adhesion of the adhesive 5 to the component surface in that part 3a therefore is good.

Now the test procedure can be continued in a corresponding state as shown in FIG. 1 and described above. Because of the reduced adhesion at the second of the first parts 3b, 3c seen from right, a complete detachment of the adhesive 5 from that part 3b takes place. The state obtained by that is illustrated in FIG. 7. As the test procedure continues further, the adhesion of the adhesive 5 can now be tested at the second of the second parts 3a (seen from right).

Figure 4:
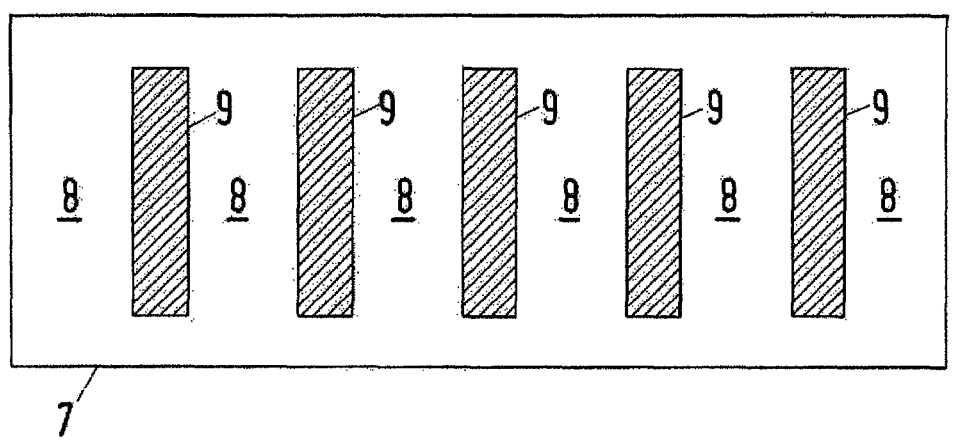
FIG. 4 is a top view of a stencil with five parallel strip-shaped holes.

FIG. 4 shows the top view of a stencil 7. The stencil 7 is composed of a layer of material of even thickness and has five strip shaped holes 9 disposed parallel with one another and at constant distance one to another. Disposed between and beside the holes 9 are material areas 8 of the stencil. The stencil 7, as other stencils also, can be prepared, e.g., by punching the holes from a sheet or panel material.

If the material of the stencil 7 is an anti-adhesion material, the stencil can be arranged on a component surface such that its material covers the component surface in first parts whereas the holes 9 leave second parts of the component surface exposed. Then adhesive can be applied to the stencil in the longitudinal direction going from left to right in FIG. 4 or in the opposite direction so that the adhesive extends over the holes 9. The arrangement of the adhesive in FIG. 4, particularly in relation to the holes 9, can be the same as the arrangement of the adhesive 5 in FIG. 3 in relation to the anti-adhesion material strips, i.e., an adhesive bead extends in a longitudinal direction over the holes 9 and the anti-adhesion material strips, respectively.

The illustration in FIG. 4, as also the illustrations in the other figures, should be taken to be schematic, however. The dimensions and the number of the anti-adhesion material areas and the holes may vary. In particular, it is preferred that the length of the holes 9 (measured in longitudinal direction from left to right in FIG. 4) relative to the material areas 8 between the holes 9 of the stencil 7 is greater than shown in FIG. 4.

Unlike the illustration in FIG. 1 and FIG. 2, the component 1 can have at its surface several layers of different materials, wherein the uppermost material layer provides the component surface. For example, the component is composed of a carrying substrate provided on which at first, as seen from the substrate to the component surface, is a priming coat, on top of that an intermediate paint coat and again on top of that a top coat layer. Optionally disposed on the top coat layer can also be a layer of an adhesion-promoting agent which improves the adhesion of the adhesive to the component surface.

We claim:

1. A method for testing the adhesion of elastic adhesives or elastic sealing materials on surfaces of components comprising of the following steps:
   a) applying the adhesive or the sealing material to a component surface of a component,
   b) optionally curing the adhesive or sealing material,
   c) attempting, by exerting a peeling force, to detach the applied adhesive or the applied sealing material from the component surface, and
   d) assessing the adhesion of the adhesive or the sealing material on the basis of fractures caused in the adhesive or the sealing material by the exertion of the peeling force and the detachment of the adhesive or the sealing material from the component surface by the exertion of the peeling force wherein
   prior to and/or during step a), an anti-adhesion material layer is applied to at least one first part of the component surface, which causes poorer adhesion of the adhesive or the sealing material to the component surface and therefore the adhesive or the sealing material can be detached from the component surface with less peeling force than directly from the component surface and the adhesive or the sealing material in step a) is applied as a continuous material section both to the at least one first part of the component surface to which the anti-adhesion material layer is applied and directly to at least one second part of the component surface, wherein the adhesive or the sealing material is applied to the component surface in such a way that the adhesive or the sealing material extends in a longitudinal direction at least from one of the second parts over an intervening one of the first parts to one of the second parts.

2. The method as claimed in claim 1, wherein the adhesive or the sealing material is applied to the component surface in such a way that the adhesive or the sealing material extends, in the longitudinal direction, over first and second parts of the component surface disposed alternately in succession.

3. The method as claimed in claim 2, wherein the distances of the first parts defined by the dimensions of the second parts in the longitudinal direction are of the same size.

4. The method as claimed in claim 1, wherein the at least one second part of the component surface is formed by a layer of an adhesion-promoting substance which improves the adhesion of the adhesive or the sealing material to the component.

5. The method as claimed in claim 1, wherein the anti-adhesion material layer is removed from the component surface completely and without residue and wherein then adhesive or sealing material of the same type is again applied to the first and second parts and in this way an adhesive bond or a seal between two components is produced.

6. The method as claimed in claim 1, wherein again adhesive or sealing material of the same type is applied to other parts of the component surface than the first and second parts and in this way an adhesive bond or a seal between two components is produced.

7. An arrangement for testing the adhesion of elastic adhesives or elastic sealing materials to surfaces of components, with adhesive or sealing material applied to a component surface of a component, comprising an anti-adhesion material layer because of which the adhesion of the adhesive or the sealing material to the component surface is poorer and the adhesive or sealing material can therefore be detached from the component surface by applying a lower peeling force than directly from the component surface, wherein the adhesive or the sealing material is applied, as continuous material section, both to at least one first part of the component surface with anti-adhesion material layer between the adhesive and the component surface and also directly to at least one second part of the component surface without anti-adhesion material layer, wherein the adhesive or the sealing material is applied to the component surface in such a way that the adhesive or the sealing material extends in a longitudinal direction at least from one of the second parts over an intervening one of the first parts to one of the second parts.

8. The arrangement as claimed in claim 7, wherein the adhesive or the sealing material is applied to the component surface in such a way that the adhesive or the sealing material extends, in the longitudinal direction, over first and second parts of the component surface disposed alternately in succession.

9. The arrangement as claimed in claim 8, wherein the distances of the first parts defined by the dimensions of the second parts in the longitudinal direction are of the same size.

* * * * *